US009645115B2

(12) United States Patent
Tanabe et al.

(10) Patent No.: US 9,645,115 B2
(45) Date of Patent: May 9, 2017

(54) QCM SENSOR

(71) Applicant: SEIKO INSTRUMENTS INC., Chiba (JP)

(72) Inventors: Sachiko Tanabe, Chiba (JP); Masayuki Suda, Chiba (JP); Hiroshi Muramatsu, Tokyo (JP)

(73) Assignee: SEIKO INSTRUMENTS INC. (JP)

( * ) Notice: Subject to any disclaimer, the term of this patent is extended or adjusted under 35 U.S.C. 154(b) by 502 days.

(21) Appl. No.: 14/099,262

(22) Filed: Dec. 6, 2013

(65) Prior Publication Data
US 2014/0165702 A1 Jun. 19, 2014

(30) Foreign Application Priority Data

Dec. 17, 2012 (JP) ................................. 2012-274508
Sep. 6, 2013 (JP) ................................. 2013-185293

(51) Int. Cl.
*G01N 29/036* (2006.01)
*G01N 29/02* (2006.01)

(52) U.S. Cl.
CPC . *G01N 29/022* (2013.01); *G01N 2291/02818* (2013.01)

(58) Field of Classification Search
CPC ......... G01N 2291/0256; G01N 29/036; G01N 29/022; G01N 5/02; G01N 2291/0255; G01N 2291/02818; G01N 29/222; G01N 11/16; G01N 1/405; G01N 2291/02809; G01N 29/4427; G01N 33/0004; G01G 3/16; G01G 3/18; H03B 5/32; H03H 2003/0428; H03H 2003/0435; H03H 2003/0471;

(Continued)

(56) References Cited

U.S. PATENT DOCUMENTS

2001/0008081 A1* 7/2001 Smith ...................... G01G 3/13
73/19.03
2009/0293590 A1* 12/2009 Zeng .................... G01N 29/022
73/24.06

(Continued)

FOREIGN PATENT DOCUMENTS

JP         2004205392 A  *  7/2004

OTHER PUBLICATIONS

Patent Abstracts of Japan, Publication No. 2004-205392, Publication Date Jul. 22, 2004.

*Primary Examiner* — Daniel S Larkin
(74) *Attorney, Agent, or Firm* — Adams & Wilks

(57) ABSTRACT

A QCM sensor for detecting a physical quantity of a sample includes a quartz crystal vibrator for measurement, a quartz crystal vibrator for reference, and a housing accommodating the quartz crystal vibrator for measurement and the quartz crystal vibrator for reference. The quartz crystal vibrator for measurement has a first electrode that is contacted by a measurement sample to be detected, and a first quartz substrate provided with a surface on which the first electrode is formed. The quartz crystal vibrator for reference has a second electrode that is contacted by a reference sample as a reference when detecting a physical quantity of the measurement sample, and a second quartz substrate provided with a surface on which the second electrode is formed. A confining portion connects to the housing to confine the reference sample in a state of contacting the second electrode.

18 Claims, 13 Drawing Sheets

(58) Field of Classification Search
CPC ........... H03H 3/04; H03L 1/022; H03L 1/028; H03L 1/04; H03L 2224/16245; H02N 2/001
See application file for complete search history.

(56) References Cited

U.S. PATENT DOCUMENTS

| | | | |
|---|---|---|---|
| 2010/0021346 A1* | 1/2010 | Wakamatsu | G01N 5/02 422/69 |
| 2010/0088039 A1* | 4/2010 | Yang | C07K 1/20 702/23 |
| 2010/0313636 A1* | 12/2010 | Wakamatsu | G01N 29/022 73/64.53 |
| 2011/0064614 A1* | 3/2011 | Watanabe | G01G 3/13 422/69 |
| 2011/0316522 A1* | 12/2011 | Shinobu | G01N 5/02 324/109 |

* cited by examiner

QCM SENSOR

BACKGROUND OF THE INVENTION

Field of the Invention

The present invention relates to a QCM (Quartz Crystal Microbalance) sensor for measuring physical properties by using vibration of a quartz crystal vibrator.

Background Art

In the case of measuring a minute physical quantity of a sample to be measured by a quartz crystal vibrator by using a QCM sensor, an absolute value of the physical quantity is extremely small, therefore, it has been difficult to secure the measurement accuracy. Accordingly, a means for grasping a physical quantity by comparison with a measured value of a reference sample is known (JP-A-2004-205392 (Patent Document 1)). In such related-art technique, a QCM sensor in which a quartz crystal vibrator measuring a measurement sample and a quartz crystal vibrator measuring a reference sample are arranged on the same support base is used to compare measured values of both samples.

However, as the related-art QCM sensor has a structure in which the quartz crystal vibrator for measurement and the quartz crystal vibrator for reference are separately arranged, it is difficult to secure same atmosphere of measurement. Moreover, as the quartz crystal vibrator for measurement and the quartz crystal vibrator for reference are separately accommodated, the measurement environment of both crystal vibrators may differ, therefore, it may be difficult to secure the accuracy of comparative measurement.

SUMMARY OF THE INVENTION

The present invention has been made in view of the above, and an object thereof is to provide a QCM sensor capable of detecting the physical quantity of the measurement sample accurately, when measurement is perfomed by immersing the QCM sensor into the sample atmosphere.

The present invention provides the following means for achieving the above object.

That is, a QCM sensor according to the invention detects a physical quantity of a sample by allowing the sample to contact an excitating electrode on a surface of a quartz crystal vibrator. The QCM sensor includes a quartz crystal vibrator for measurement having a first electrode which is in contact with a measurement sample to be detected and a first quartz substrate in which the first electrode is formed on a surface, a quartz crystal vibrator for reference having a second electrode which is in contact with a reference sample when detecting the physical quantity of the measurement sample and a second quartz substrate in which the second electrode is formed on a surface, a housing accommodating the quartz crystal vibrator for measurement and the quartz crystal vibrator for reference, and a confining portion to confine the reference sample in a state of contacting the second electrode into the housing.

The above QCM sensor can detect a minute physical quantity of the measurement sample accurately when measurement is performed with the QCM sensor immersed into sample atmosphere. That is, the difference of measurement environment can be reduced by arranging the quartz crystal vibrator for reference and the quartz crystal vibrator for measurement so as to be close to each other, and the measurement condition of the reference sample can be also maintained stable. Accordingly, stable measurement result of the reference sample can be secured and inaccuracy caused by a difference in measuring condition in a comparison between reference and sample measurement result results can be suppressed as small as possible.

Also in the above QCM sensor, the housing may have a higher thermal conductivity than the reference sample.

As a temperature change which occurs outside the housing can be quickly transmitted to the reference sample in the QCM sensor, the difference in temperature between the sample atmosphere and the reference sample can be reduced. Accordingly, the temperature of the reference sample can be almost same as the measurement sample in the environment outside the housing, therefore, comparative measurement can be performed more accurately.

Also in the above QCM sensor, the housing may have a higher thermal conductivity than the quartz crystal vibrator for measurement and for reference.

As a temperature change which occurs outside the housing can be quickly transmitted to the quartz crystal vibrator in the QCM sensor, the difference in temperature between quartz crystal vibrators for measurement and for reference is extremely small. Accordingly, inaccuracy caused by a difference of measuring condition in a comparison between reference and sample measurement results can be suppressed as small as possible.

Also in the above QCM sensor, the confining portion may be formed inside an outline of the quartz crystal vibrator for reference when seen from a direction perpendicular to the surface of the quartz crystal vibrator for reference.

This means a reduction in the entire capacity of the reference sample, therefore, heat capacity of the reference sample can be reduced. Accordingly, the temperature response of the reference sample can be increased. As a result, inaccuracy caused by a temperature difference in a comparison between reference and sample measurement results can be suppressed, because of the temperature difference between the reference sample and measurement sample which exists outside the housing. Moreover, as the reference sample can be tightly enclosed by forming a lid inside the outline of the quartz crystal vibrator for reference, a stable measurement result of the reference sample can be secured.

Also in the above QCM sensor, the confining portion may be formed in an opening of the housing so as to confine the reference sample within a thickness of the housing wall when seen from a direction parallel to the surface of the quartz crystal vibrator for reference.

Therefore, the volume of the reference sample can be reduced, and the heat capacity can be suppressed to be small as well. Accordingly, when the temperature of the measurement sample at the outside of housing and the quartz crystal vibrator for measurement contacting the measurement sample is changed, the temperature of the quartz crystal vibrator for reference will become the same as both of them quickly because the reference sample has small heat capacity. As a result, an inaccuracy caused by a temperature difference in a comparison between reference and sample measurement results can be suppressed as small as possible.

Also in the above QCM sensor, a third electrode is formed on a surface of the first quartz substrate, which is opposite to the surface where the first electrode is formed, and a fourth electrode is formed on a surface of the second quartz substrate, which is opposite to the surface where the second electrode is formed may be included, and the housing may be formed so as to accommodate the third electrode and the fourth electrode in a common space.

As the third electrode and the fourth electrode are accommodated in the common (same environmental) space in the QCM sensor, electrodes of the first and the second quartz substrate, which do not contact with the sample, are put under the same condition, therefore, inaccuracy in a comparison between reference and sample measurement results can be suppressed as small as possible.

Also in the above QCM sensor, the quartz crystal vibrators for measurement and for reference may be arranged so that the third electrode faces the fourth electrode. Additionally, the housing may support both quartz crystal vibrators so that the third electrode and the fourth electrode have a predetermined gap therebetween.

This arrangement provides that the quartz crystal vibrators for measurement and for reference can be oscillated without interference with each other. Accordingly, comparative measurement can be performed more accurately. As the quartz crystal vibrators for measurement and for reference are arranged so that the third electrode faces the fourth electrode, the entire size of the QCM sensor can be reduced, therefore, temperature distribution in the QCM sensor becomes smaller, and a comparative measurement can be performed more accurately.

Also in the above QCM sensor, the reference sample is in an initial state of the measurement sample, and is encapsulated into the confining portion.

In this configuration, the reference sample can be used as a standard sample for calibration of the QCM sensor, therefore, it is possible to eliminate errors due to individual difference in characteristics of quartz crystal vibrators.

The above QCM sensor may further include a comparator which derives a difference between an output value obtained from the quartz crystal vibrator for measurement and an output value obtained from the quartz crystal vibrator for reference. The comparator derives the difference at predetermined time intervals.

In this configuration, comparative measurement becomes easier and changes of the measurement sample characteristics with time passing can be traced.

Also in the above QCM sensor, a float may be included in the housing. As the QCM sensor has the float, the first quartz substrate measuring the measurement sample can be constantly kept in a nearly same depth from a fluid level, and a pressure applied to the first quartz substrate can be stably kept even when the amount of the fluid varies. Accordingly, the measurement accuracy can be stabilized regardless of the amount of the measurement sample, and the measurement can be performed more accurately.

Also in the above QCM sensor, the first quartz substrate and the second quartz substrate may be arranged at different positions from each other when seen from a direction perpendicular to the substrate surface. Accordingly, it is possible to draw out signal wires from one side of the housing, therefore, electrical noise caused by complicated wire routing can be suppressed.

Also in the above QCM sensor, the housing consists of a first housing part accommodating the quartz crystal vibrator for measurement and a second housing part accommodating the quartz crystal vibrator for reference. Accordingly, a mutual arrangement between the quartz crystal vibrators for measurement and for reference can be easily adjusted. Adjusting a distance between them by using spacers becomes unnecessary, and the distance is determined at manufacturing of the housing, therefore, the QCM sensor which is excellent in mass productivity can be provided.

Also in the above QCM sensor, at least one of the first quartz substrate and the second quartz substrate may be bonded to the housing by a siloxane bond. Accordingly, the quartz crystal vibrator can be easily fixed to the housing without disturbing vibration of the quartz crystal vibrator. As an additional connecting part between the quartz crystal vibrator and the housing, such as an adhesive agent, is eliminated, vibration variations of the quartz crystal vibrator caused by interference of the connecting part can be suppressed and inaccuracy of measurement can be reduced. Moreover, the fixing of the quartz crystal vibrators to the housing can be simplified, thereby an unintended vibration mode is suppressed. In addition, sufficient vibration of the quartz crystal vibrator for effective detection of the physical quantity is secured even when the vibrating quartz crystal vibrators are fixed into the housing.

Also in the above QCM sensor, the physical quantity may be related to a viscosity variation of the measurement sample.

The above QCM sensor can detect minute viscosity variation of the measurement sample when it is immersed into the measurement sample whose viscosity changes with time passing.

Also in the above QCM sensor, the reference sample may be an engine oil used for lubricating engine parts. The above QCM sensor is immersed into the engine oil inside the engine, thereby accurately detecting degradation of the engine oil.

Also in the above QCM sensor, the housing may be formed on a tip side of an oil gauge so as to measure the engine oil condition easily.

Also in the above QCM sensor, the reference sample may be an initial state liquid before yeast is added. Also in the above QCM sensor, many housings enclosing the reference sample are formed in different depths inside a fermenter. As the above QCM sensor can detect variation of the fermented liquid condition, appropriate management/adjustment of the fermented liquid can be performed.

Also in the above QCM sensor, the reference sample may be a resist solution used for manufacturing semiconductors. Accordingly, precise management of a resist film thickness is realized not based on viscosity at receiving but at using, therefore, it is possible to form the film thickness more suitable for designed value.

It is possible to detect the minute physical quantity of the measurement sample accurately when measurement is perfomed by immersing the QCM sensor into the sample atmosphere.

That is, the difference in measurement condition can be reduced by arranging the quartz crystal vibrators for reference and for measurement close to each other, and the reference sample contacting with the quartz crystal vibrator for reference can be stable with time passing. Accordingly, inaccuracy in a comparison between reference and sample measurement results can be suppressed as small as possible.

Figure 13:
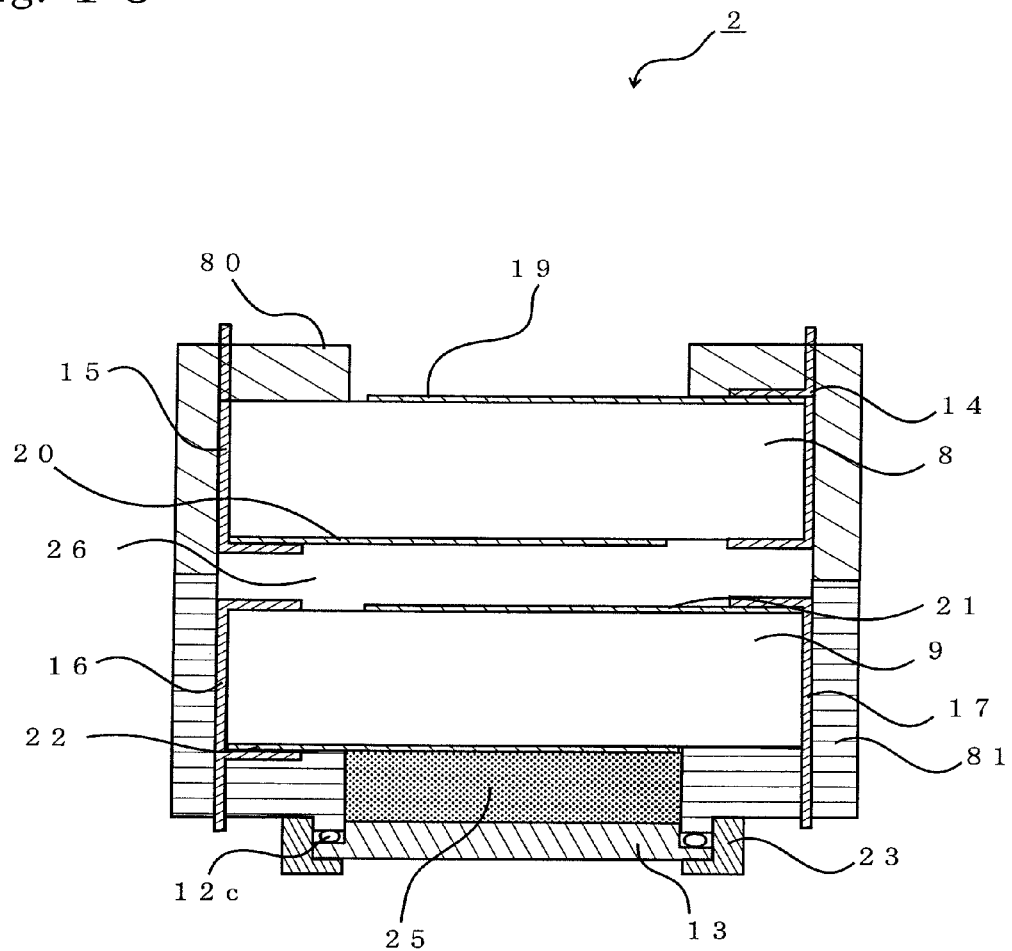

An upper drawing of FIG. 11 is a cross-sectional view in a fourth embodiment. A lower drawing of FIG. 11 is a cross-sectional view cut along a segment A-A' shown in the upper drawing and seen from a direction of an arrow B;

FIG. 12 is an exploded perspective view of a QCM sensor body according to a fifth embodiment shown; and FIG. 13 is a cross-sectional view of the QCM sensor according to the fifth embodiment.

DESCRIPTION OF THE PREFERRED EMBODIMENTS

First Embodiment

Figure 2:
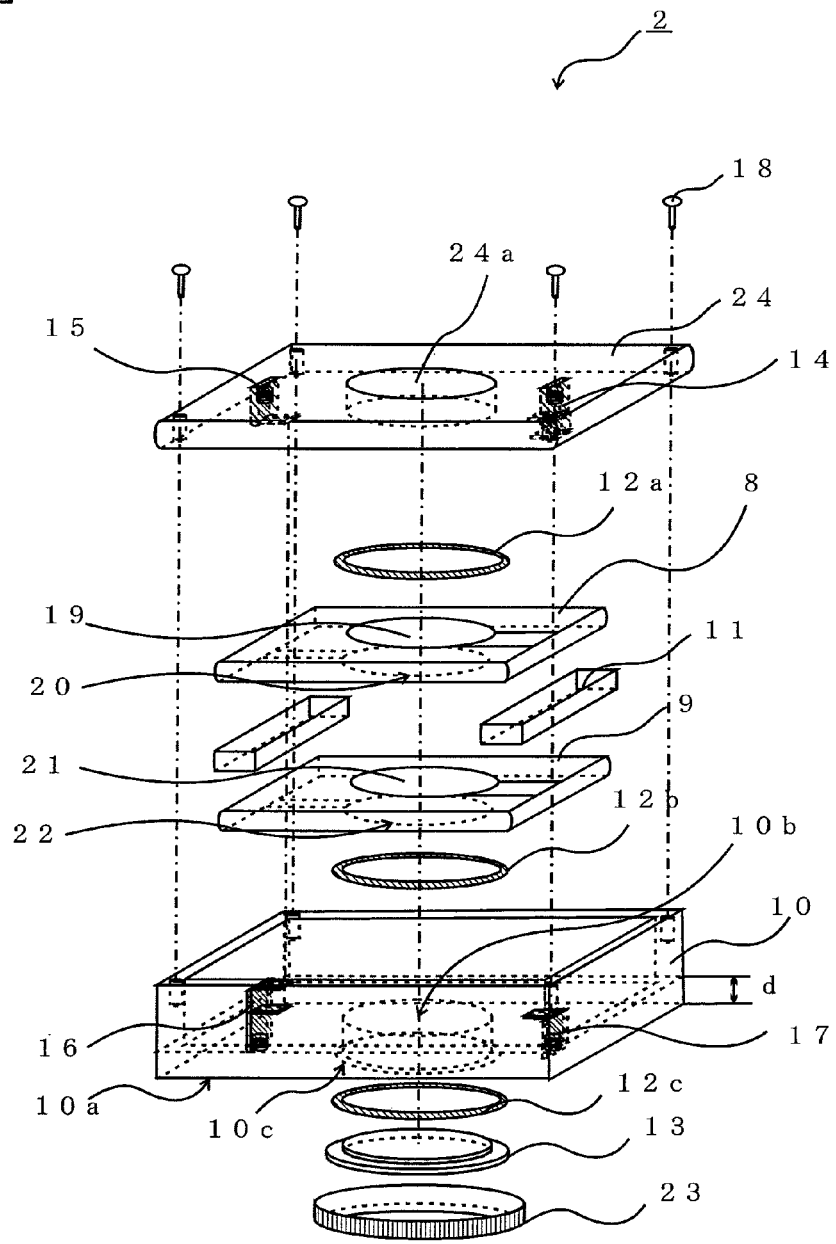
FIG. 2 is an exploded perspective view showing the QCM sensor according to the first embodiment of the present invention.
Figure 3:
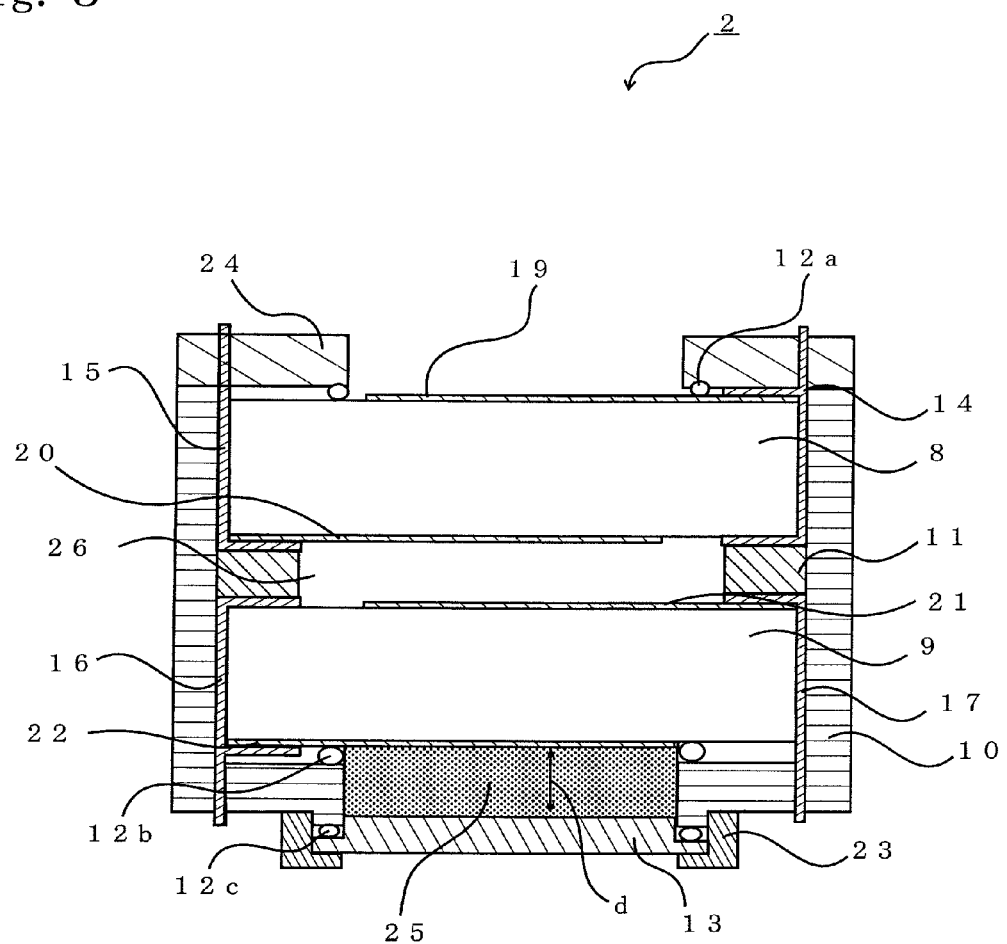
FIG. 3 is a cross-sectional view of the QCM sensor according to the first embodiment of the present invention.

Hereinafter, a QCM sensor according to a first embodiment the present invention will be explained with reference to FIG. 1 to FIG. 3 as well as FIG. 5 to FIG. 7.

Figure 1:
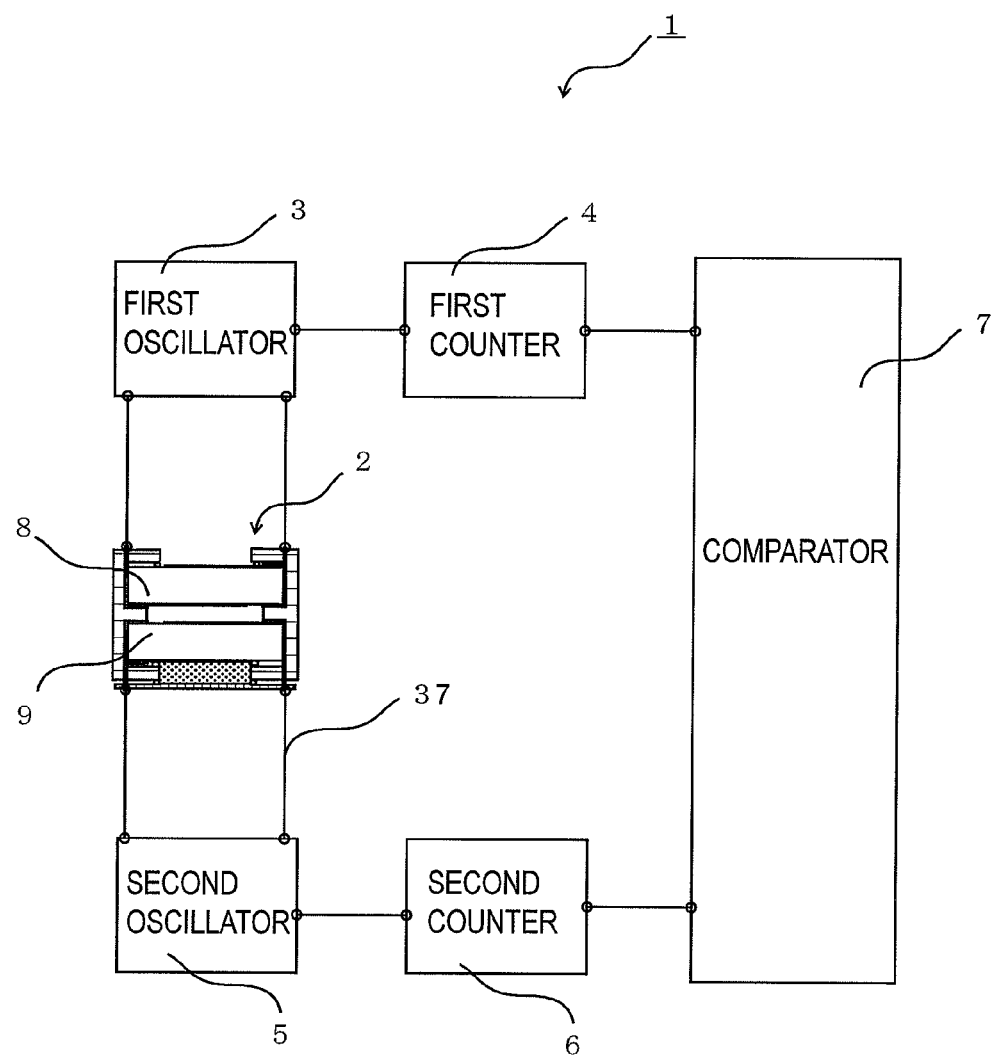
FIG. 1 is an overall structure diagram of a QCM sensor according to a first embodiment of the present invention.

FIG. 1 is an overall structure diagram showing a QCM sensor 1 according the first embodiment to the present embodiment. The QCM sensor 1 includes a QCM sensor body 2, a first oscillator 3, a first counter 4, a second oscillator 5, a second counter 6 and a comparator 7. The QCM sensor 1 includes a quartz crystal vibrator for measurement having a first quartz substrate 8 and a quartz crystal vibrator for reference having a second quartz substrate 9, and the quartz crystal vibrator for measurement is connected to the first oscillator 3. The quartz crystal vibrator for reference is connected to the second oscillator 5. The first oscillator 3 is connected to the first counter 4 and the second oscillator 5 is connected to the second counter 6, respectively. The first counter 4 and the second counter 6 are both connected to the comparator 7, comparing vibration characteristics by comparing output values from the quartz crystal vibrator for measurement and the quartz crystal vibrator for reference.

Next, a detailed structure of the QCM sensor body 2 according to the present embodiment will be explained with reference to FIG. 2 and FIG. 3. FIG. 2 is a perspective view showing the QCM sensor body 2 in an exploded manner. FIG. 3 is a cross-sectional view of the QCM sensor body 2. The QCM sensor body 2 includes the first quartz substrate 8 included in the quartz crystal vibrator for measurement for measuring a measurement sample, the second quartz substrate 9 included in the quartz crystal vibrator for reference for measuring a reference sample to be a reference at the time of detecting a physical quantity of the measurement sample, a casing 10, a lid portion 24, spacers 11, O-rings 12a, 12b and 12c, a flange (a flange lid) 13, a flange ring 23 and screws 18. A housing is formed by including the casing 10, the lid portion 24 and the spacer 11.

The first quartz substrate 8 and the second quartz substrate 9 are formed by AT-cut quartz crystal vibrators which are cut so as to excite thickness slip vibration. The first quartz substrate 8 includes a first electrode 19 on one surface and a third electrode 20 on the opposite surface, which can vibrate the first quartz substrate 8 by applying voltage between both electrodes. The first electrode 19 and the third electrode 20 have the same shape which is a shape in which a rectangular shape is added to a circular shape and formed at the same position so as to sandwich the first quartz substrate 8. In the present embodiment, rectangular portions are extended in opposite directions. The first electrode 19 and the third electrode 20 are made of a metal film using a titanium thin film as a base. The component material of these electrodes is not limited to the above, and metal films which can stably vibrate the AT-cut quartz crystal vibrators may be used. Similarly, the second quartz substrate 9 includes a second electrode 22 on one surface and a fourth electrode 21 on the opposite surface, which can vibrate the second quartz substrate 9 by applying voltage between both electrodes. Respective electrodes are connected to respective oscillators by lead electrodes, and respective lead electrodes include a first lead electrode 14, a second lead electrode 15, a third lead electrode 16 and a fourth lead electrode 17. The first lead electrode 14 is formed in a C-shape sandwiching the quartz crystal vibrator for measurement from both faces in the thickness direction, and similarly, the third lead electrode 16 is formed in a C-shape sandwiching the quartz crystal vibrator for reference from both faces in the thickness direction. The first lead electrode 14 and the second lead electrode 15 are connected to the electrodes of the quartz crystal vibrator for measurement. The third lead electrode 16 and the fourth lead electrode 17 are connected to the electrodes of the quartz crystal vibrator for reference. The first lead electrode 14 is electrically connected to the first electrode 19 contacting the measurement sample and the second lead electrode 15 is electrically connected to the third electrode 20. The quartz crystal vibrator for measurement is supported by the first lead electrode 14 and the second lead electrode 15 so as to be sandwiched from both right and left side faces. The first lead electrode 14 and the second lead electrode 15 are further supported by an inner peripheral surface of the casing 10. Therefore, the quartz crystal vibrator for measurement is supported by the casing 10 through the first lead electrode 14 and the second lead electrode 15. Here, as the first lead electrode 14 and the second lead electrode 15 are formed only at part of the whole circumference of the quartz crystal vibrator for measurement, the minimum area is occupied by the first lead electrode 14 and the second lead electrode 15 with respect to the casing 10 as a housing in a circumferential direction of the quartz crystal vibrator for measurement. As the quartz crystal vibrator for measurement is supported with respect to the casing 10 by these lead electrodes connected to the quartz crystal vibrator for measurement, the quartz crystal vibrator for measurement can be supported with respect to the casing 10 without arranging any particular support member. Accordingly, the quartz crystal vibrator for measurement can be vibrated with minimum interruption as well as electrical conduction of the quartz crystal vibrator for measurement can be stably secured.

Similarly, the quartz crystal vibrator for reference is supported by the casing 10 through the third lead electrode 16 and the fourth lead electrode 17. The third lead electrode 16 is electrically connected to the second electrode 22 contacting a reference sample, and the fourth lead electrode 17 is electrically connected to the fourth electrode 21. Here, as the third lead electrode 16 and the fourth lead electrode 17 are not formed only at part of the whole circumference of the quartz crystal vibrator for reference, the minimum area is occupied by the third lead electrode 16 and the fourth lead electrode 17 with respect to the casing 10 as the housing in a circumferential direction of the quartz crystal vibrator for reference. As the quartz crystal vibrator for reference is supported with respect to the casing 10 by these lead electrodes connected to the quartz crystal vibrator for reference, the quartz crystal vibrator for reference can be supported without arranging any particular support member. Accordingly, the quartz crystal vibrator for reference can be vibrated with minimum interruption as well as electrical conduction of the quartz crystal vibrator for reference can be stably secured. The housing accommodating the quartz crystal vibrator for measurement and the quartz crystal vibrator for reference inside is configured by including the lid portion 24 and the spacers 11 in addition to the above casing 10.

The spacers 11 are housed inside the casing 10 in addition to the above quartz crystal vibrator for measurement and the quartz crystal vibrator for reference. The spacers 11 are used for keeping an interval between the first quartz substrate 8 and the second quartz substrate 9 or between the first lead electrode 14 and the fourth lead electrode 17 and between the second lead electrode 15 and the third lead electrode 16, which are made of a material having excellent insulating performance and chemical resistance. For example, nitrile rubber and so on can be used. An isolation layer 26 as a space sandwiched by the quartz crystal vibrator for measurement and the quartz crystal vibrator for reference is formed by the spacers 11 and the volume of the isolation layer 26 is prescribed. The thickness of the spacers 11 is formed to be equal to or more than a distance so as not to be affected by respective vibrations of the respective quartz crystal vibrator for measurement and the quartz crystal vibrator for reference, which is at least 1 μm (micrometer) or more. The isolation layer 26 arranges the third electrode 20 of the quartz crystal vibrator for measurement and the fourth electrode 21 of the quartz crystal vibrator for reference in a common space. In the case where the spacers 11 are formed so as to keep the interval between the first lead electrode 14 and the fourth lead electrode 17 as well as the interval between the second lead electrode 15 and the third lead electrode 16, it is possible to avoid a situation in which the spacers 11 directly supports the quartz substrates. Here, in the first lead electrode 14 and the third lead electrode 16 formed in the C-shape, one of two edges formed in approximately parallel as edges forming the C-shape may be connected to the first electrode 19 and the second electrode 22 formed on opposite surfaces of the isolation layer 26 relating to the quarts substrates, and the other edge may be formed so as to be held with a gap with respect to the first quarts substrate 8 or the second quartz substrate 9. In this case, the spacers 11 can be configured so as to contact the other electrodes of these lead electrodes having the C-shape and not to contact the quartz substrates, therefore, the interruption in vibration of the quartz substrates can be reduced.

Additionally, the first lead electrode 14 and the fourth lead electrode 17 are formed in the same thickness and the second lead electrode 15 and the third lead electrode 16 are also formed in the same thickness. Moreover, the third electrode 20 and the fourth electrode 21 are formed in the same thickness. Therefore, even when positions where the facing second electrode 20 and the fourth electrode 21 are lead out by the lead electrodes are opposite to each other, the distance between the second electrode 20 and the fourth electrode 21 can be uniform by allowing the thickness of the spacers 11 to be uniform. Accordingly, the isolation layer 26 can be stably secured. The isolation layer 26 is formed so as to be surrounded by the spacers 11, the first quartz substrate 8 and the second quartz substrate 9. The isolation layer 26 can also adjust the volume appropriately by changing the thickness of the spacers 11. The thickness and the volume are reduced to thereby allow the third electrode 20 of the quartz crystal vibrator for measurement and the fourth electrode 21 of the quartz crystal vibrator for reference to be close to each other, and allow the environment of both units to be closer to the same. Accordingly, as it is possible to reduce the difference in environment under which electrodes other than the electrodes used for measurement are placed in the quartz crystal vibrator for measurement and the quartz crystal vibrator for reference, comparison and measurement can be performed more accurately.

The casing 10 is a recessed box having the depth in which the O-rings 12a and 12b, the first quartz substrate 8, the spacers 11 and the second quartz substrate 9 can be accommodated with a bottom portion 10a as a bottom face. On the bottom portion 10a, the O-ring 12b, the quartz crystal vibrator for reference having the second quartz substrate 9, the spacers 11, the quartz crystal vibrator for measurement having the first quartz substrate 8 and the O-ring 12a are stacked in this order, and the lid portion 24 is placed on the O-ring 12a. The lid portion 24 is attached to the casing 10, and the O-ring 12a and the O-ring 12b are compressed by the lid portion 24 and the bottom portion 10a of the casing 10, thereby supporting the quartz crystal vibrator for reference and the quartz crystal vibrator for measurement with respect to the housing.

Additionally, a hole 10b is opened in the bottom portion 10a so that a electrode portion of the second electrode 22 is seen therefrom. The hole 10b is a through hole piercing the bottom portion 10a, and the depth thereof, namely, a thickness "d" of the bottom portion 10a is preferably as thin as possible, which is preferably 5 mm or less. Accordingly, the reference sample contacting the second electrode 22 can be accommodated with a small quantity, which can reduce heat capacity of the reference sample. As temperature variation (temperature change) of the measurement sample can be transmitted to the entire reference sample earlier even when the QCM sensor body 2 exists in an atmosphere of the measurement sample, the temperature difference between the measurement sample and the reference sample and temperature variation of the reference sample can be suppressed as small as possible. As a result, a factor other than variation in characteristics of the measurement sample and the reference sample, which is the temperature difference, can be eliminated, therefore, comparison and measurement can be performed more accurately. Moreover, the third lead electrode 16 and the fourth lead electrode 17 respectively connected to the second electrode 22 and the fourth electrode 21 are provided on both sides of the hole 10b, thereby electrically connecting the second quartz substrate 9 to the outside. On an outer face on the opposite side of the bottom portion 10a of the hole 10b, a convex portion 10c is formed so as to surround the hole 10b. The convex portion 10c is threaded, and a flange ring 23 is fitted thereto by screw clamping.

Here, the casing 10 is preferably made of a material having a high thermal conductivity as well as excellent insulating performance and chemical resistance. In particular, as the casing 10 is made of a material having a higher thermal conductivity than the measurement sample, the reference sample 25, the quartz crystal vibrator for measurement and the quartz crystal vibrator for reference, the temperature variation of the samples or the quartz substrates can be transmitted earlier at the time of measurement, therefore, the temperature of the entire QCM sensor body 2 can be uniformly maintained. Accordingly, the factor other than variation in characteristics of the measurement sample and the reference sample 25, which is the difference in thermal environment, can be eliminated as much as possible, therefore, comparison and measurement can be performed more accurately. A thermal conductivity of crystal is 8 W/m·K (watt/meter·Kelvin), and a thermal conductivity of an oil type is generally less than 1 W/m·K when the reference sample is the oil type, therefore, the thermal conductivity of the casing 10 is preferably more than 10 W/m·K. The casing 10 is preferably made of a material whereby the reference sample 25 hardly causes oxidative degradation. An initial state of the reference sample 25 can be maintained by using the casing material whereby the reference sample 25 hardly causes oxidative degradation. Accordingly, when variations caused with time by the measurement sample are measured, the measurement of variations can be performed more accurately. As specific materials, for example, alumina ceramics having a thermal conductivity of 32 W/m·K, silicon carbide having a thermal conductivity of 100 to 350 W/m·K, a material obtained by depositing thermally-oxidized thin film on a silicon material having a thermal conductivity of 168 W/m·K and so on can be used.

The O-rings 12a and 12b are respectively provided at the first electrode 19 and the second electrode 22, which are formed to be slightly larger than the circular shape of the electrodes. The O-ring 12c is provided at the convex portion 10c of the casing 10, which is formed to be the same circular shape as the circular shape of the convex portion 10c. As the O-rings (seals) 12a to 12c (12a, 12b, and 12c) have a sealing function for preventing the entry and leakage of the samples to and from the inside of the housing 10, the O-rings 12a to 12c are preferably made of a rubber material having excellent insulating performance and chemical resistance. For example, nitrile rubber and so on can be used. The quartz crystal vibrator for measurement and the quartz crystal vibrator for reference are configured so as to be held in the thickness direction with respect to the housing by the O-ring 12a and the O-ring 12b as described above. Accordingly, the quartz crystal vibrator for measurement and the quartz crystal vibrator for reference are fixed to the housing only by the O-rings and the lead electrodes so that both quartz crystal vibrators can be vibrated with minimum interruption. Therefore, the measurement with given accuracy can be realized. Here, parts used at positions where the O-rings 12a to 12c are arranged are not necessarily O-rings. Members having the sealing function of preventing the samples from flowing in or flowing out which are equivalent to the O-rings, and functional materials having excellent insulating performance and chemical resistance and whereby both quartz crystal vibrators can be vibrated with minimum interruption can be used as seals. For example, a silicone resin sealant which can be applied in a cream state may be used. In the case of using the silicone resin sealant, the sealant is applied to portions where the O-rings are applied.

The lid portion 24 is for closing an opening (aperture) of the casing 10, which is formed to be a plate shape similar to an outline of the casing 10. A circular opening (aperture) 24a is formed so that the first electrode 19 is seen therefrom in the center of the lid portion 24, and the first lead electrode 14 and the second lead electrode 15 are further provided so as to sandwich the opening 24a. The first lead electrode 14 and the second lead electrode 15 are respectively connected to the first electrode 19 and the third electrode 20, which can electrically connect the first quartz substrate 8 to the outside. Additionally, four corners are fixed by clamping the lid portion 24 and the casing 10 by the screws 18. The lid portion 24 is preferably made of a material having a high thermal conductivity as well as excellent insulating performance and chemical resistance in the same manner as the casing 10. In particular, as the lid portion 24 is made of the material having a higher thermal conductivity than thermal conductivities of the measurement sample, the reference sample 25, the quartz crystal vibrator for measurement and the quartz crystal vibrator for reference, temperature variation of the samples or the quarts substrates can be transmitted earlier at the time of measurement, therefore, the temperature of the whole QCM sensor body 2 can be uniformly maintained. Accordingly, the factor other than variation in characteristics of the measurement sample and the reference sample 25, which is the difference in thermal environment, can be eliminated as much as possible, therefore, comparison and measurement can be performed more accurately. The thermal conductivity of crystal is 8 W/m·K, and a thermal conductivity of the oil type is generally less than 1 W/m·K when the reference sample is the oil type, therefore, the thermal conductivity of the casing 10 is preferably more than 10 W/m·K. The lid portion 24 is preferably made of a material whereby the reference sample 25 hardly causes oxidative degradation. The initial state of the reference sample 25 can be maintained by using the lid portion material whereby the reference sample 25 hardly causes oxidative degradation. Accordingly, when variations caused with time in the measurement sample are measured, the measurement of variations can be performed more accurately. As specific materials, for example, alumina ceramics having the thermal conductivity of 32 W/m·K, silicon carbide having the thermal conductivity of 100 to 350 W/m·K, a material obtained by depositing thermally-oxidized thin film on a silicon material having the thermal conductivity of 168 W/m·K and so on can be used.

The flange 13 is fixed so as to close the hole 10b of the casing 10 by the flange ring 23, which is formed in a disk shape having a convex portion to be fitted to the hole 10b. The flange 13 and the flange ring 23 are made of the same material as the casing 10, for example, alumina ceramics and so on are preferably used. The flange 13 and the flange ring 23 form a confining portion for confining the reference sample. The flange 13 as the confining portion, the hole 10b as part of the housing, the O-ring 12b and the second electrode 22 form a space in which the reference sample 25 is confined. As part of the flange 13 is fitted to the hole 10b, the thickness of the volume in which the reference sample is enclosed is formed to be thinner than the thickness "d" of the bottom portion 10a of the casing 10 due to a portion entering the inside of the hole 10b of the flange 13. Accordingly, the reference sample 25 can be stored with a small quantity, which can reduce temperature unevenness of the reference sample 25 to be compared at the time of measurement. The O-ring 12b not only elastically supports the bottom portion 10a of the casing 10 and the quartz crystal vibrator for reference but also functions as a seal for preventing leakage of the reference sample 25. That is, the O-ring 12b have both functions of supporting the quartz crystal vibrator for reference while permitting vibration of the quartz crystal vibrator for reference and preventing the leakage of the reference sample. A diameter of the hole 10b as a side face of the volume in which the reference sample 25 is accommodated is positioned inside a plane of the second quartz substrate 9 forming the quartz crystal vibrator for reference. Accordingly, the reference sample 25 accommodated inside the hole 10b can be small in quantity.

(Method of Assembling QCM Sensor)

Next, a method of assembling the QCM sensor body 2 according to the embodiment will be explained with reference to FIG. 2 and FIG. 3. FIG. 3 is a cross-sectional view in an assembled state of the QCM sensor body 2. First, the second quartz substrate 9 is provided on the bottom portion 10a with the O-ring 12b sandwiched therebetween. When the silicone resin sealant is used instead of the O-ring 12b, the silicone resin sealant is applied to the portion where the O-ring 12b is arranged. The second quartz substrate 9 is provided so that the second electrode 22 and the fourth electrode 21 electrically contact the third lead electrode 16 and the fourth lead electrode 17 provided in the casing 10 respectively. Next, the spacers 11 are provided so as not to overlap the circular portions of the fourth electrode 21 and the third electrode 20, and the first quartz substrate 8 is subsequently provided. The first quartz substrate 8 is provided so that the first electrode 19 and the third electrode 20 electrically connect to the first read electrode 14 and the second lead electrode 15 respectively. The spacers 11 are sandwiched between the first quartz substrate 8 and the second quartz substrate 9 as described above, thereby providing the isolation layer 26 between the first quartz substrate 8 and the second quartz substrate 9. Accordingly, as the third electrode 20 of the first quartz substrate 8 and the fourth electrode 21 of the second quartz substrate 9 are included in the same environment, measurement values obtained on the third electrode 20 and the fourth electrode 21, namely, measurement noise can be cancelled when measurement values obtained by measuring samples on the other respective first electrode 19 and the second electrode 22, therefore, comparison and measurement between the first quartz substrate 8 and the second quartz substrate 9 can be performed with high accuracy. Next, the O-ring 12a is provided so as to surround the first electrode 19, and the lid portion 24 is subsequently placed so that the first electrode 19 is seen from the opening 24a, then, four corners of the lid portions 24 are fixed to the casing 10 by the screws 18. When the silicone resin sealant is used instead of the O-ring 12a, the silicone resin sealant is applied to the portion where the O-wing 12a is arranged. Next, the casing 10 is placed so that the bottom portion 10a of the casing 10 faces upward, and the reference sample 25 is injected in to the hole 10b. When the silicone resin sealant is used instead of the O-rings 12a and 12b, the reference sample 25 is injected after the silicone resin sealant is sufficiently dried. After the hole 10b is filled with the reference sample 25, the flange 13 is placed with the O-ring 12c being sandwiched, then, the flange ring 23 is fastened to thereby enclose the reference sample 25. When the silicone resin sealant is used instead of the O-ring 12c, the silicone resin sealant is applied to the portion where the O-ring 12c is arranged. In this case, the reference sample 25 is injected to the full capacity so that the reference sample 25 contacts the surface of the second electrode 22 in the state where the QCM sensor body 2 is place so that the flange 13 side faces downward. Here, the capacity of the reference sample 25 is reduced when the above-described thickness "d" of the bottom portion 10a is allowed to be thin, therefore, in the case where the temperature in environment under which the entire QCM sensor body 2 is placed varies, the temperature of the reference sample 25 can follow the temperature under the environment of the QCM sensor body 2 due to heat propagated from the casing 10, the flange 13 and so on having high thermal conductivity.

(Measurement Method by QCM Sensor)

Subsequently, operations of the QCM sensor 1 according to the first embodiment will be explained.

First, the QCM sensor body 2 is dipped in the measurement sample and preparation for measurement is performed. The measurement sample exists as the sample atmosphere of liquid or gas, and the QCM sensor body 2 according to the embodiment is used in such sample atmosphere. At this time, the reference sample 25 is already enclosed in a state of contacting the second electrode 22 of the second quartz substrate, and the measurement sample and the reference sample are completely isolated. Accordingly, the measurement sample and the reference sample are not mixed in the sample atmosphere, therefore, comparison and measurement of both samples can be accurately performed. The measurement sample enters from the opening 24a of the lid portion 24 onto a surface where the first electrode 19 exists in the first quartz substrate 8, and the measurement sample contacts the first electrode 19. However, the measurement sample does not enter further inside the casing 10 due to the O-ring 12a. Next, AC voltage is respectively applied to the first quartz substrate 8 and the second quartz substrate 9 by the first oscillator 3 and the second oscillator 5. A first output value and a second output value of the first quartz substrate 8 and the second quartz substrate 9 respectively obtained by applying the voltage are compared by the comparator 7 to thereby obtain a comparison value.

Next, a QCM sensor system on which the QCM sensor body 2 according to the present embodiment is mounted will be explained with reference to FIG. 5.

Figure 5:
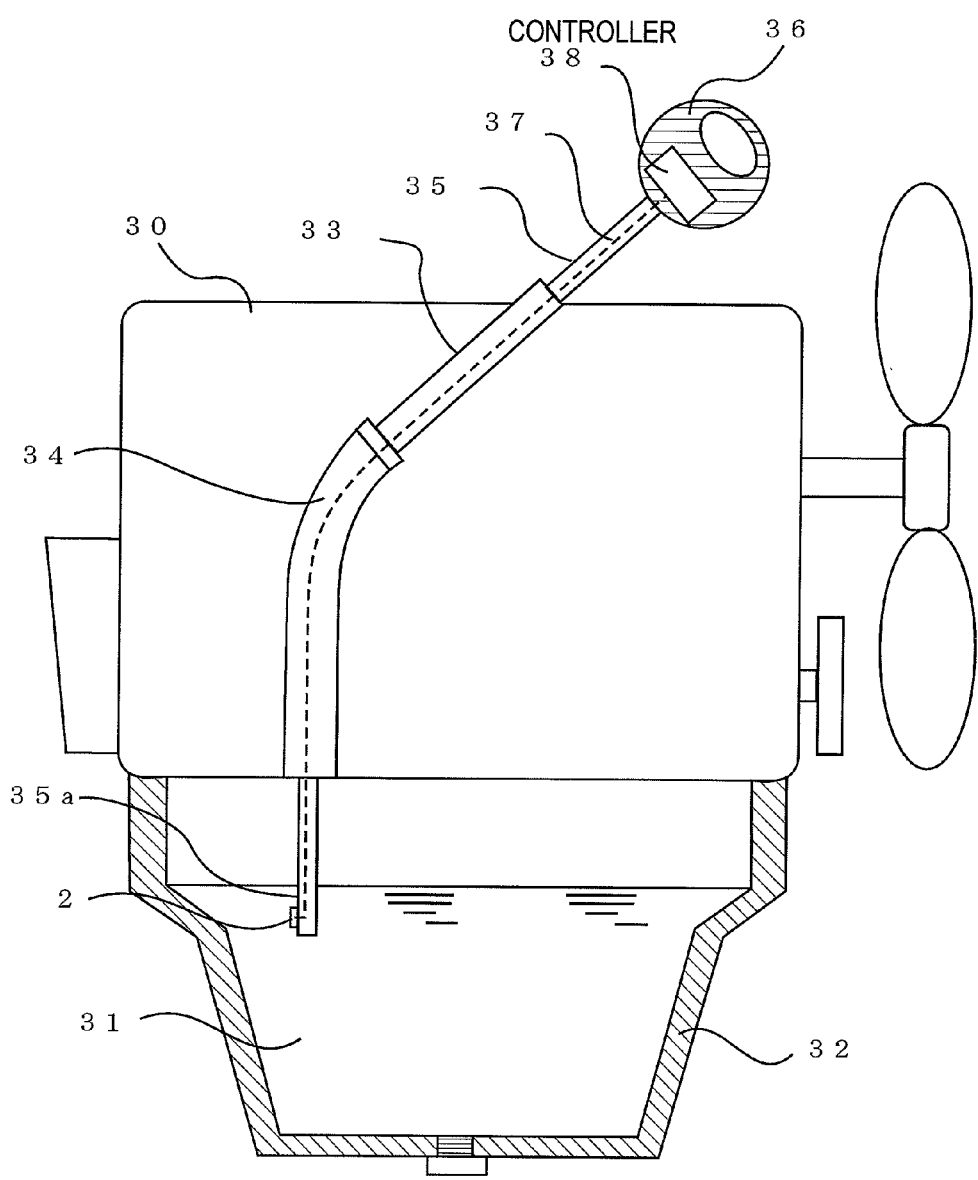
FIG. 5 is a schematic diagram of periphery of the engine to which the QCM sensor according to the first embodiment is attached.

FIG. 5 is a structure diagram of an engine to which the QCM sensor 1 according to the embodiment is attached and the periphery thereof. An oil pan 32 accommodating an engine oil 31 is attached below an engine 30. The engine 30 includes an oil level gauge 33, a guide tube 34 fixedly installed on a side part of the engine 30, a tip portion of which communicating into the engine 30 and an oil level stick 35 inserted into the guide tube 34, a tip portion 35a of which reaches an oil surface of the engine oil 31.

The QCM sensor body 2 is attached to the tip portion 35a of the oil level stick 35, and the entire QCM sensor body 2 is dipped into the engine oil 31 as the sample atmosphere. A wiring 37 connected to the above lead electrodes is connected from the QCM sensor body 2, and the wiring 37 is extended to a handle portion 36 at a base end of the oil level stick 35 along the oil level stick 35. The handle portion 36 is provided with a controller 38 including the first oscillator 3, the first counter 4, the second oscillator 5, the second counter 6, the comparator 7 which are shown in FIG. 1 and a power supply, and the controller 38 is electrically connected to the QCM sensor body 2 by the wiring 37.

(Method of Measuring Viscosity)

Next, a method of measuring viscosity by the QCM sensor according to the embodiment will be explained. The explanation will be made by citing the above engine oil 31 as an example of a measurement target of viscosity.

First, the engine oil in an initial state (brand-new engine oil) is enclosed in the QCM sensor body 2 as the reference sample 25, and the oil level stick 35 is inserted into the engine oil 31 in the same initial state as the reference sample 25. At this time, the QCM sensor body 2 is in a state of being dipped in the engine oil 31. A comparison measurement value C[0] is obtained in the initial state. At this time, the comparison measurement value C[0] is a ratio of resonant frequencies respectively measured by the first counter 4 and the second counter 6. As the reference sample 25 and the engine oil 31 in the initial state as the measurement sample are the same sample, the comparison measurement value C[0] should be ideally "1". Accordingly, calibration is performed by setting the comparison measurement value C[0] to "1". Next, the engine 30 is normally used. When the engine 30 is used, the engine oil 31 is circulated in the engine 30 and gradually deteriorated as well as varies in condition. The condition variation due to the deterioration caused by use of the engine oil 31 can be monitored by acquiring comparison measurement values C[n] (n=1, 2, 3 . . . ) of both quartz crystal vibrators at regular intervals. Here, temperatures of the engine oil 31 at the time of measurement are preferably the same in both points of C[0] and C[n]. The acquired measurement data may be processed so as to be displayed in the vicinity of the controller 38 as well as may be processed to be displayed at a short distance apart from the engine 30 by transmitting data wirelessly.

Next, a fermenter on which the QCM sensor 1 according to the present embodiment is mounted will be explained with reference to FIG. 6 and FIG. 7. A measuring method of the following respective QCM sensors is the approximately the same as the above measuring method.

Figure 6:
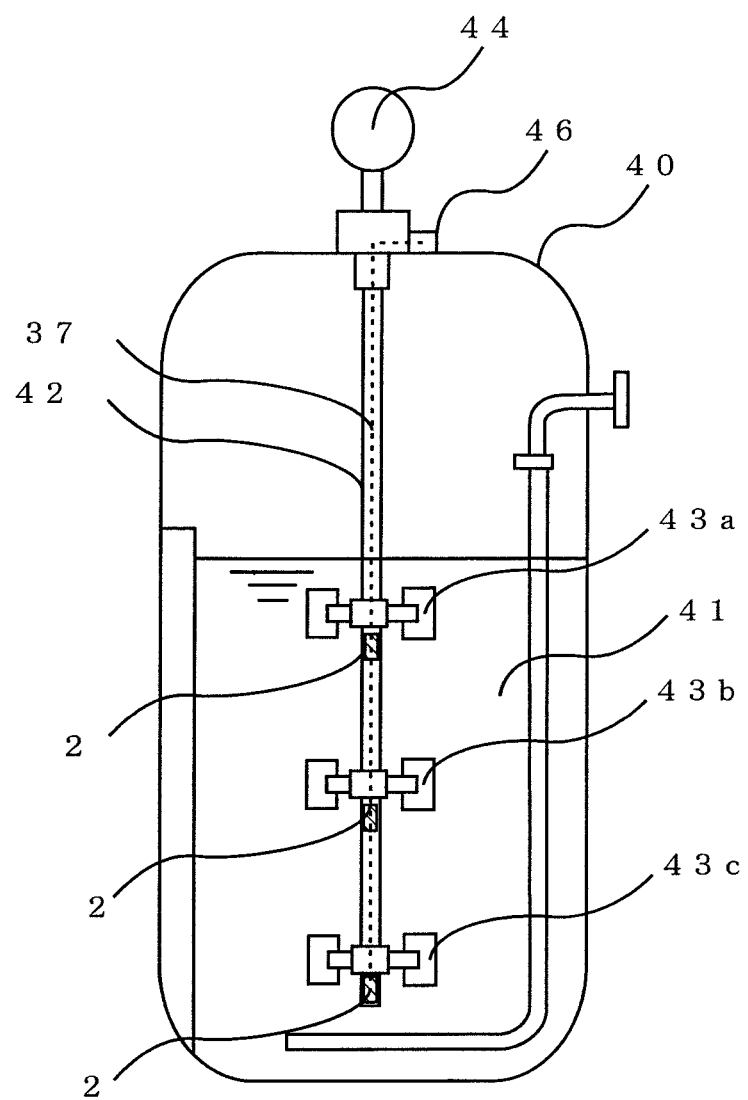
FIG. 6 is a structure diagram of a fermenter to which the QCM sensor according to the first embodiment is attached.

FIG. 6 is a structure diagram of a fermenter 40 on which the QCM sensor 1 according to the embodiment is mounted. A reference fermented liquid is enclosed in the QCM sensor body 2 as the reference sample 25. The reference fermented liquid is an organic compound to which yeast is not added as an initial state of the fermented liquid. The fermenter 40 includes a fermented liquid 41 including fermented foodstuffs such as brewed beverage like sake, vinegar, miso and soy sauce, or alcohol used for biological experiments and lactic acid, a rotary shaft 42 and disk turbine blades 43a, 43b and 43c provided at the rotary shaft 42 in three tiers. The disk turbine blades 43a, 43b and 43c are rotated by a motor 44 to thereby stir the fermented liquid 41. Plural QCM sensor bodies 2 are attached to respective vicinities of the disk turbine blades 43a, 43b and 43c in the rotary shaft 42, which are electrically connected to a controller 46 provided on an upper portion of the fermenter 40 by the wiring 37.

Figure 7:
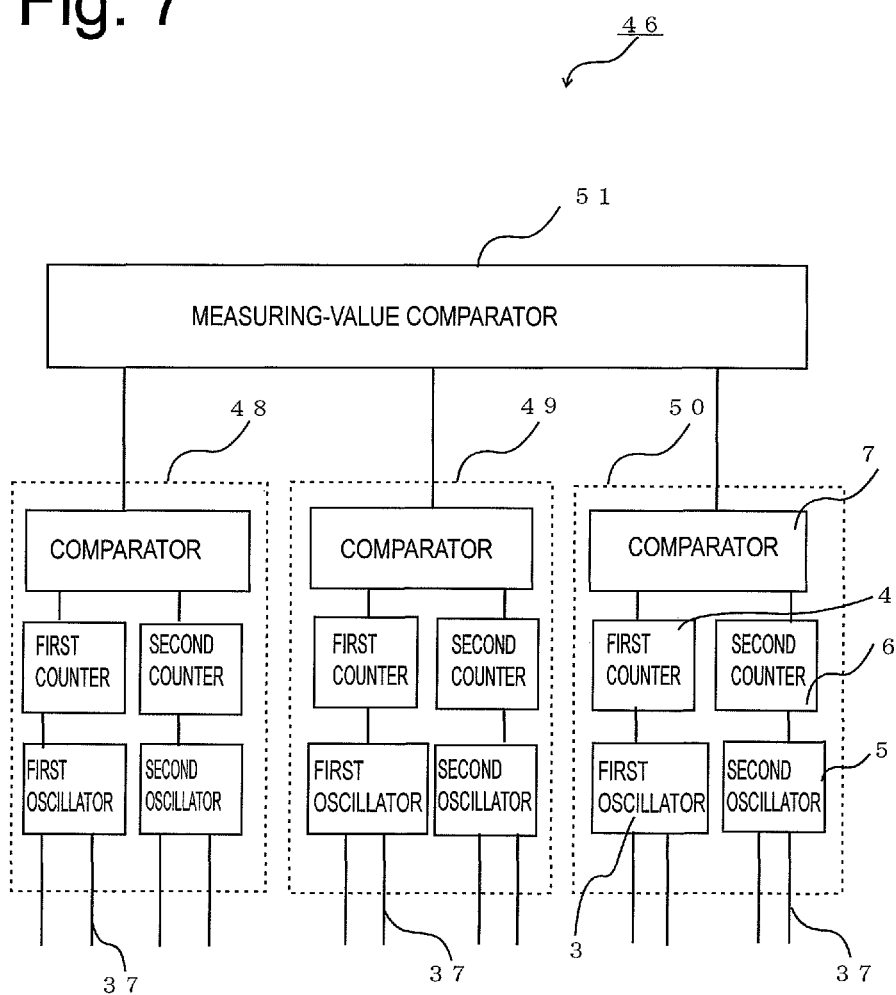
FIG. 7 is a structure diagram of a controller for the QCM sensor according to the first embodiment which is attached to the engine or the fermenter.

FIG. 7 is a diagram showing the controller 46. The controller 46 includes respective measuring units 48, 49 and 50 measuring vibration characteristics to be obtained from the plural QCM sensor bodies 2 and a measuring-value comparator 51. The respective measuring units 48, 49 and 50 are provided with the first oscillator 3, the first counter 4, the second oscillator 5, the second counter 6 and the comparator 7 (refer to FIG. 1), which can calculate comparison measurement values C1, C2 and C3 of respective QCM sensor bodies 2. The measuring-value comparator 51 compares these three comparison measurement values C1, C2 and C3.

As described above, the plural QCM sensors are attached at respective depths of the fermenter 40, and the comparison measurement values C1, C2 and C3 obtained by the plural QCM sensors are further compared by the measuring-value comparator 51, thereby monitoring state variation of the fermented liquid 41 due to fermentation at respective measurement points as well as knowing variations in the state of the fermented liquid 41 in respective depths. Accordingly, the disk turbine blades 43a, 43b and 43c can be used for stirring the fermented liquid 41 so that the state of the fermented liquid 41 in respective depths inside the fermenter 40 becomes uniform. Here, it is preferable to measure temperatures at respective measurement points at the measurement.

(Hydraulic Oil Sensor)

Figure 8:
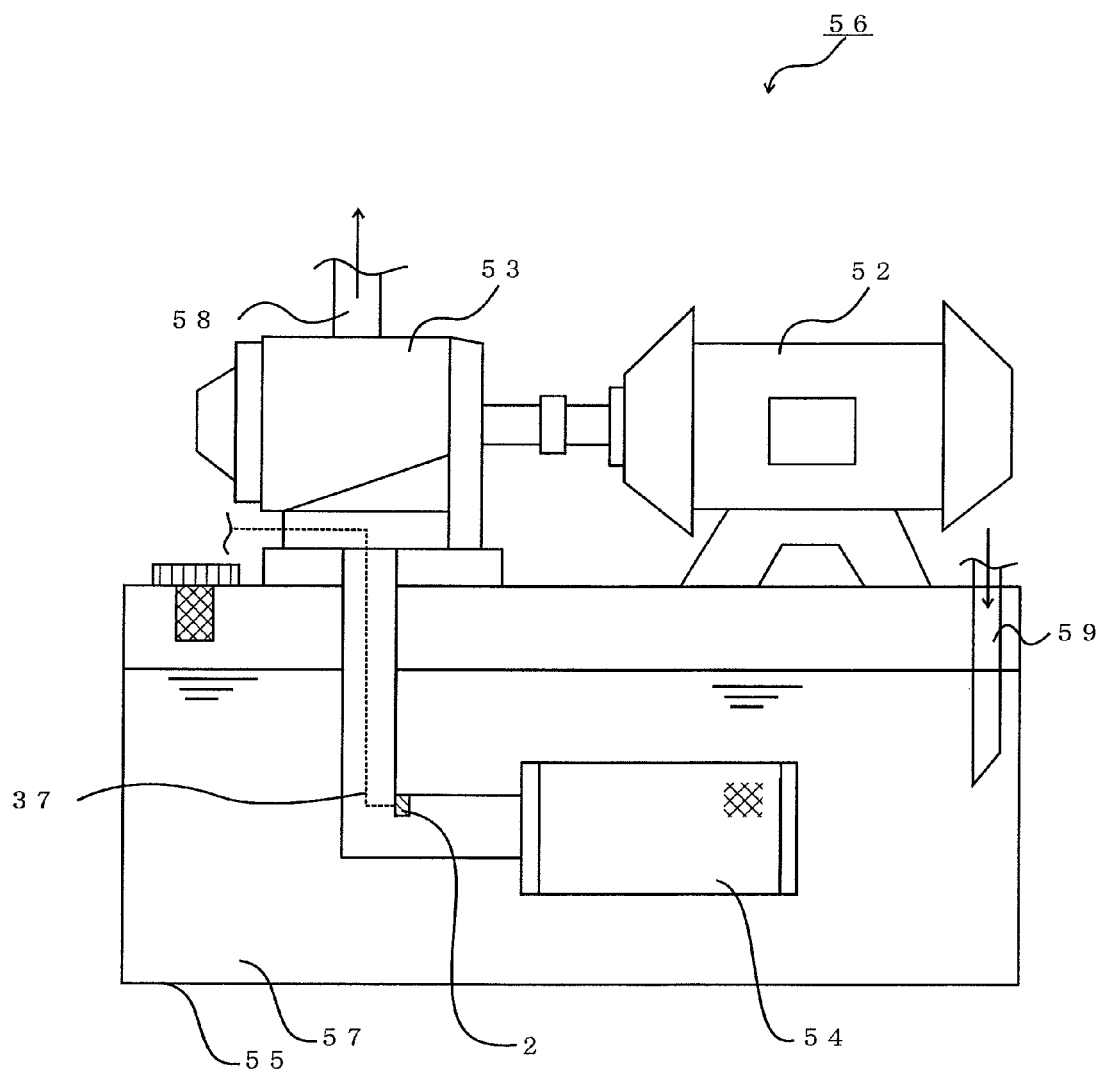
FIG. 8 is a structure diagram of a pump unit to which the QCM sensor according to the first embodiment is attached.

Next, a structure in a case where the QCM sensor 1 according to the first embodiment is used by being mounted on a pump unit for a hydraulic pump will be explained with reference to FIG. 8. FIG. 8 is a structure diagram of a pump unit 56. The pump unit 56 includes an electric motor 52, a pump 53, a strainer 54 and an oil tank 55. The inside of the oil tank 55 is filled with a hydraulic oil 57. The hydraulic oil 57 is absorbed from the oil tank 55 to the pump 53, discharged from a discharge port 58 and returns to the oil tank 55 again from a return pipe 59. The hydraulic oil 57 returned to the oil tank 55 is fed to the pump 53 again after removing refuse by the strainer 54.

The QCM sensor body 2 is provided on the downstream of the strainer 54 so as to be completely dipped in the hydraulic oil 57 just after removing refuse by the strainer 54. The QCM sensor body 2 is preferably provided at a position where a flow velocity is 0 mm/s (millimeter/second) so as not to be affected by the flow of the hydraulic oil 57 if possible. The wiring 37 connected to the lead electrodes is connected from the QCM sensor body 2 and is extended to the outside of the oil tank 55 along the pipe. At the end of the wiring 37, a controller (not shown) including the first oscillator 3, the first counter 4, the second oscillator 5, the second counter 6, the comparator 7 shown in FIG. 1 and a power supply is installed, which is electrically connected to the QCM sensor body 2.

A method of measuring viscosity is approximately the same as the measuring method of the above example of the engine oil 31. However, only the reference sample to be used is different. As the reference sample to be enclosed in advance, the hydraulic oil 57 as a measurement target in a brand new state is used.

As described above, a small-sized QCM sensor body 2 is mounted inside the oil tank 55 and variation with time of the hydraulic oil 57 is monitored, thereby preventing failure of the pump unit 56 due to clogging of the strainer 54 and so on.

(Resist Viscosity Sensor)

Figure 9:
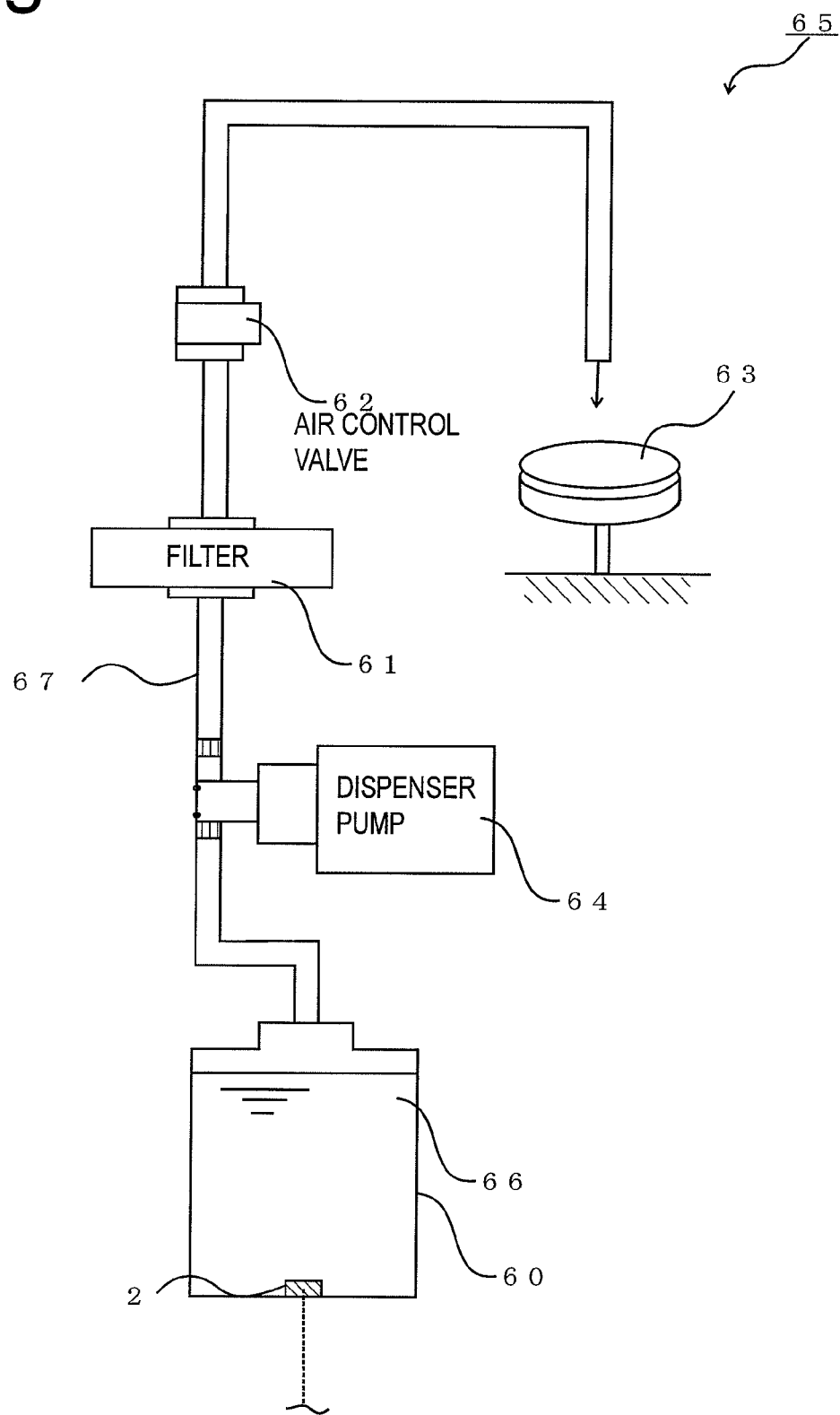
FIG. 9 is a structure diagram of a resist coating apparatus to which the QCM sensor according to the first embodiment is attached.

Next, a structure in a case where the QCM sensor 1 according to the first embodiment is used by being mounted on a resist coating apparatus used at the time of manufacturing semiconductors will be explained with reference to FIG. 9. FIG. 9 is a structure diagram simply showing a resist coating apparatus 65. The resist coating apparatus 65 includes a resist bottle 60, a dispenser pump 64, a filter 61, an air control valve 62 and a pipe 67. A resist solution 66 is accommodated inside the resist bottle 60, and the resist solution 66 is transmitted from the resist bottle 60 to the filter 61 by the dispenser pump 64, and is further applied to a surface of a wafer 63 through the air control valve 62.

The QCM sensor body 2 is provided on a bottom portion of the resist bottle 60 and is dipped in the resist solution 66. A controller (not shown) including the first oscillator 3, the first counter 4, the second oscillator 5, the second counter 6, the comparator 7 shown in FIG. 1 and a power supply is electrically connected from the QCM sensor body 2 in the resist bottle 60 to the outside along the wiring 37.

The method of measuring viscosity is approximately the same as the measuring method of the above example of the engine oil 31. However, only the reference sample to be used is different. As the reference sample to be enclosed in advance, the resist solution 66 as a measurement target in a brand new state, or a viscometer calibration standard solution which has the same viscosity under the same temperature as the resist solution 66 inside the resist bottle 60 is used. The comparison measurement value C[n] is preferably a value based on the viscosity.

When the resist solution is applied to the wafer, a film thickness of the resist is controlled according to the viscosity in many cases. In this case, variation of viscosity of the resist solution largely affects the quality of products fabricated by photolithography. Normally, the viscosity of the resist solution is used by trusting the viscosity at the time of purchase.

However, the viscosity of the resist solution 66 can be constantly managed also at the time of use by mounting the small-sized QCM sensor 2 inside the resist bottle 60. Accordingly, a fact that the viscosity of the resist solution 66 varies can be immediately known, and variations in quality and the failure can be reduced.

Second Embodiment

The QCM sensor 1 according to a second embodiment of the present invention will be explained with reference to FIG. 4. In the following explanation, the same components as the first embodiment are denoted by the same symbols and the explanation thereof is omitted.

Figure 4:
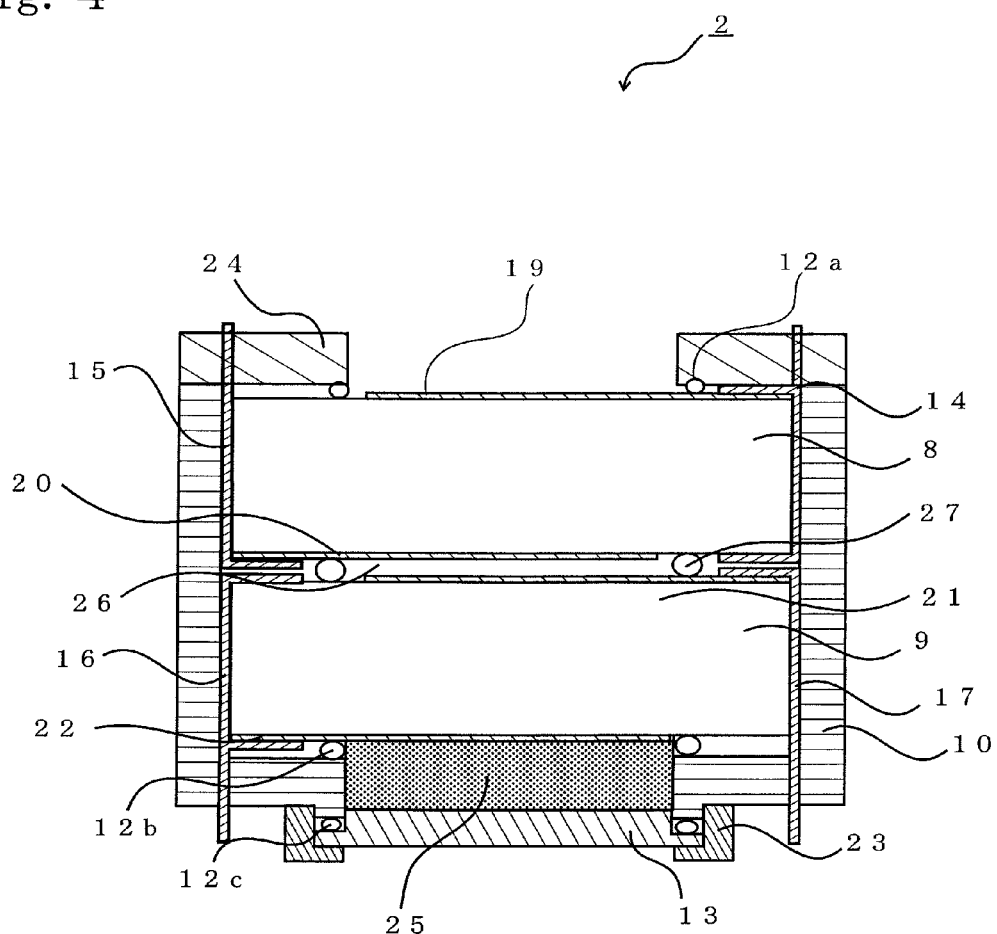
FIG. 4 is a cross-sectional view of a QCM sensor according to a second embodiment of the present invention.

FIG. 4 is a cross-sectional view showing an assembled state of the QCM sensor body 2 according to the present embodiment. The QCM sensor body 2 according to the embodiment is provided with an O-ring 27 between the first quartz substrate 8 and the second quartz substrate 9 instead of the spacers 11 (refer to FIG. 3) provided in the first embodiment. The O-ring 27 has a larger diameter than the circular portions of the third electrode 20 and the fourth electrode 21, which is used for keeping an interval between the first quartz substrate 8 and the second quartz substrate 9, an interval between the first lead electrode 14 and the fourth lead electrode 17 and an interval between the second lead electrode 15 and the third lead electrode 16. Accordingly, the O-ring 27 is formed to have a thickness thicker than at least a thickness of two lead electrodes. Additionally, the O-ring 27 is made of a material having excellent insulating performance and chemical resistance, for example, nitrile rubber and so on can be used.

As described above, the number of parts can be reduced by using the O-ring as compared with the spacers which have two parts in a pair, therefore, the QCM sensor can be easily assembled as well as intervals between respective parts can be appropriately kept, as a result, the measurement can be accurately performed.

Third Embodiment

The QCM sensor 1 according to a third embodiment of the present invention will be explained with reference to FIG. 10. In the following explanation, the same components as the first embodiment are denoted by the same symbols and the explanation thereof is omitted.

Figure 10:
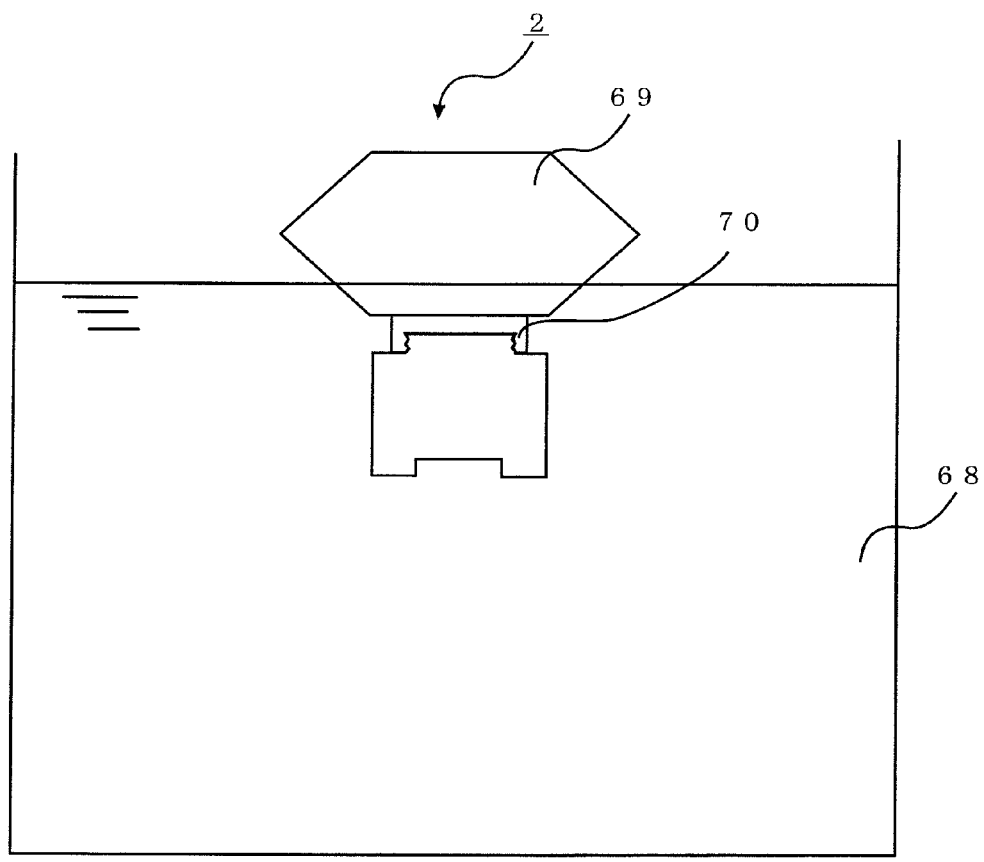
FIG. 10 is a view showing a state in which a QCM sensor body according to a third embodiment is in a measurement sample.
Figure 1:
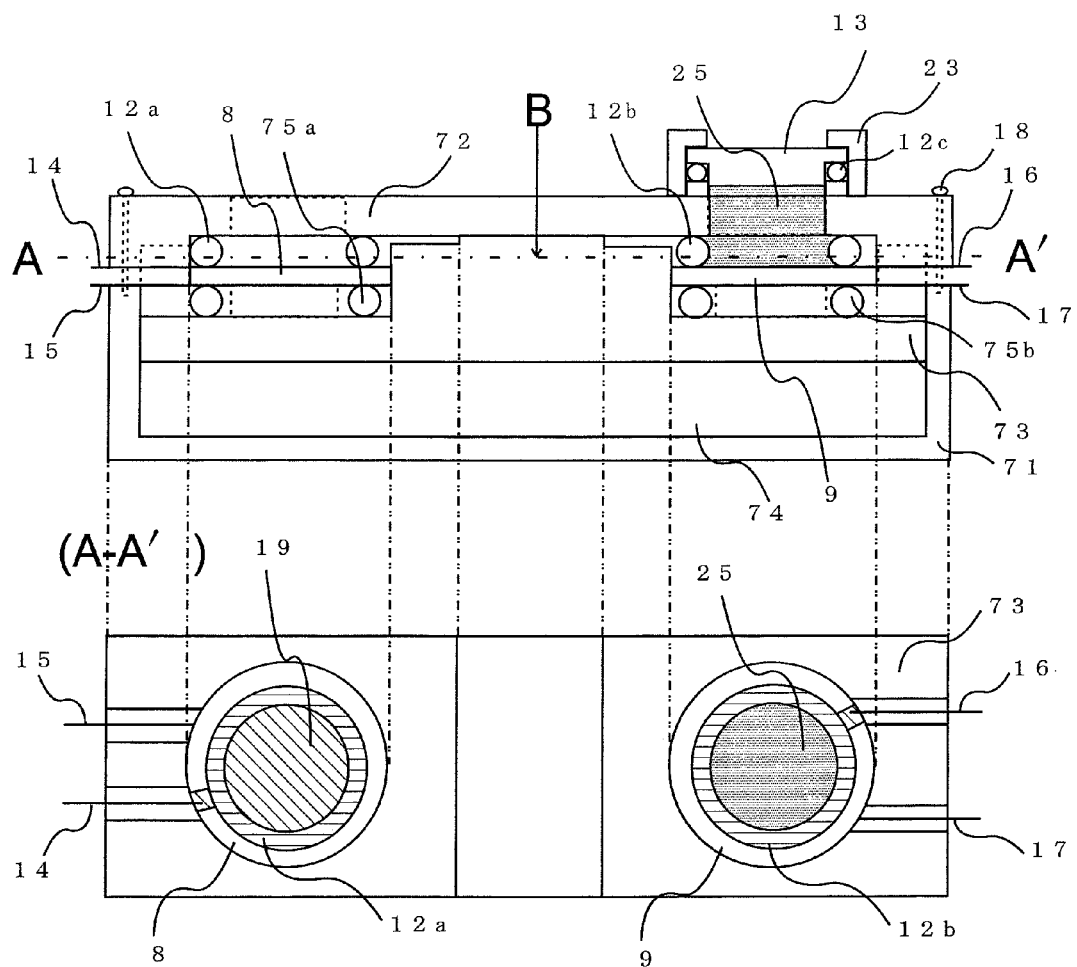
Figure 1:
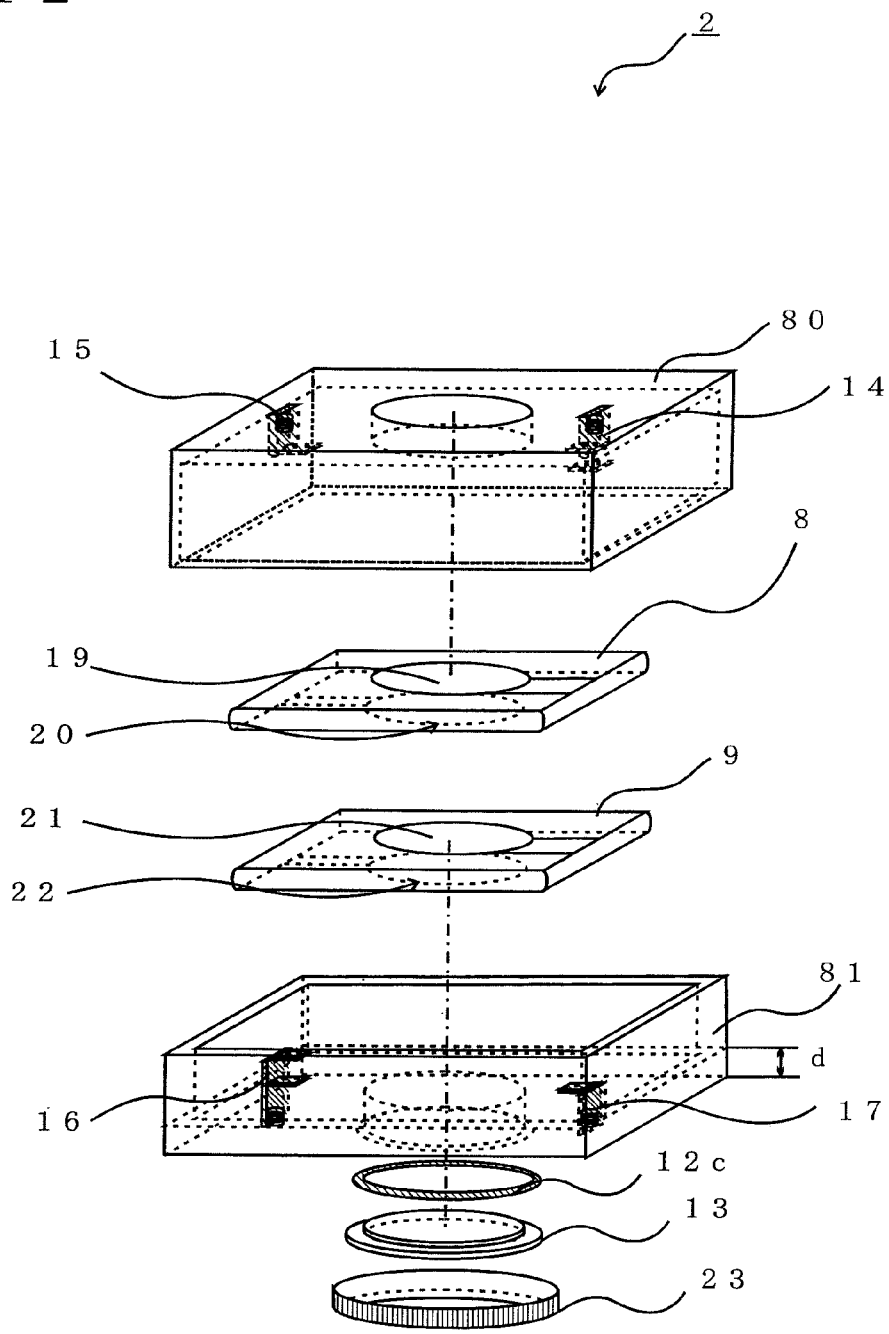

FIG. 10 is a view showing a state in which the QCM sensor body 2 according to the present embodiment is in a measurement sample 68. The QCM sensor body 2 according to the embodiment differs from the above embodiments in a point that a part for sealing the hole 10b of the casing 10 is a screw lid 70 and a float 69 is attached to the screw hole 70. The inside of the float is hollow, therefore, the QCM sensor body 2 can stay in a fixed depth from a fluid level of the measurement sample 68 due to buoyancy of the float 69 when the QCM sensor body 2 is sunk into the liquid measurement sample 68.

When the QCM sensor having the float is applied as described above, the first quartz substrate measuring the measurement sample can be constantly kept in a fixed depth from the fluid level, and a pressure applied to the first quartz substrate can be kept approximately the same even when the liquid measure varies. Accordingly, the measurement accuracy can be stabilized regardless of the remaining amount of the measurement sample 68, and the measurement can be performed more accurately. Though the housing and the float 69 are separately provided in the embodiment, the float can be incorporated with the housing. In such case, part of the housing may be changed to a member having high buoyancy, or an air-tight space can be formed in part of the housing. The member having higher buoyancy and the air-tight space are formed on the side where the reference sample of the housing is arranged in a biased manner. Accordingly, the side of the reference sample is the liquid level side of the measurement sample, and the measurement electrode (first electrode 19) side is positively held in the liquid. Therefore, the measurement accuracy can be stabilized regardless of the remaining value of the measurement sample 68.

Fourth Embodiment

The QCM sensor 1 according to a fourth embodiment of the present invention will be explained with reference to FIG. 11. In the following explanation, the same components as the first embodiment are denoted by the same symbols and the explanation thereof is omitted.

An upper drawing of FIG. 11 is a cross-sectional view of the present embodiment. A lower drawing of FIG. 11 is a cross-sectional view cut along a segment A-A' shown in the upper drawing and seen from a direction of an arrow B. The first quartz substrate 8 and the second quartz substrate 9 are arranged side by side at different positions from each other in the horizontal direction when seen from a direction perpendicular to the substrate surface, which is different from the above embodiments. The QCM sensor body 2 includes the first quartz substrate 8, the second quartz substrate 9, a casing 71, a receiver 73, a lid portion 72, O-rings 12a, 12b, 12c, 75a and 75b, the flange 13, the flange ring 23 and the screws 18. The casing 71 is a rectangular parallelepiped having an opening on one face. The receiver (bridge) 73 is arranged a given distance (at least 1 μm or more) apart from a bottom portion of the casing 71, and portions to which the first quartz substrate 8, the second quartz substrate 9, the first lead electrode 14, the second lead electrode 15, the third lead electrode 16, the fourth lead electrode 17 are fitted are concave portions (recessions). A portion where the third electrode 20 and the fourth electrode 21 are positioned forms an opening portion, and the third electrode 20 and the fourth electrode 21 are exposed in a common space 74. The receiver 73 is installed on a beam provided inside the casing 71. It is also preferable that the casing 71 is integrally formed with the receiver 73. The lid portion 72 is installed on the opposite side of the receiver 73 with the first quartz substrate 8, the second quartz substrate 9, and the O-rings 12a, 12b being sandwiched. In the lid portion 72, two points of openings are provided, from which the first electrode 19 and the second electrode 20 are respectively seen. An outer periphery of the opening from which the second electrode 20 is seen on a surface opposite to the side where the second quartz substrate 9 is provided in the lid portion 72 forms a convex portion, and an outer side face of the convex portion is threaded. On the convex portion, the O-ring 12c, the flange 13 and the flange ring 23 can be sequentially attached, and the reference sample 25 can be enclosed in a space made between the second quartz substrate 9 and the flange 13. A surface of the lid portion 72 which faces the first lead electrode 14, the second lead electrode 15, the third lead electrode 16 and the fourth lead electrode 17 form a convex portion protruding so as to sandwich the lead electrodes, thereby fixing the lead electrodes.

Next, a method of assembling the QCM sensor body 2 according to the embodiment will be explained. First, the O-ring 75a and the O-ring 75b are arranged on an outer periphery of the opening provided in the recessed portion of the receiver 73 formed in the casing 71. The first quartz substrate 8 and the second quartz substrate 9 to which the lead electrodes are attached are arranged over the O-rings so that the first electrode 19 and the second electrode 22 are respectively seen from the openings. Next, the O-ring 12a is arranged on an outer periphery of the first electrode 19 on the first quartz substrate 8. Similarly, the O-ring 12b is arranged on an outer periphery of the second electrode 22 on the second quartz substrate 9. Subsequently, the lid portion 72 is placed over the arranged O-rings, and the casing 71 and the lid portion 72 are screwed at four points by using screws 18. Subsequently, the reference sample 25 is injected from the opening from which the second electrode 22 is seen. After the inside of the opening is filled with reference sample 25, the O-ring 12c is placed on the convex portion on the outer periphery of the opening, and the opening is closed by the flange 13 to be firmly screwed by the flange ring 23.

As described above, the thickness of the housing can be reduced by arranging two quartz substrates in parallel, therefore, comparison and measurement of the measurement sample can be continuously performed even when the entire QCM sensor body is dipped into the measurement sample with a small liquid measure. Moreover, it is possible to draw out the lead electrodes from one side of the housing, not drawing out the lead electrodes from upper and lower both sides of the housing as in the above embodiments. As it is also possible to draw out the lead electrodes from a gap between the casing 71 and the lid portion 72, therefore, the wiring can be simple. It is also possible to suppress noise and so on caused by complicated wire routing. Furthermore, as the receiver is provided inside the casing as a reinforcing portion, the rigidity of the housing can be increased.

Fifth Embodiment

Next, the QCM sensor 1 according to a fifth embodiment of the present invention will be explained with reference to FIG. 12 and FIG. 13. In the following explanation, the same components as the first embodiment are denoted by the same symbols and the explanation thereof is omitted.

FIG. 12 is a perspective view of the QCM sensor body 2 according to the present embodiment shown in an exploded manner. FIG. 13 is a cross-sectional view of the QCM sensor body 2. The QCM sensor body 2 according to the embodiment includes a first casing 80 (first housing portion), a second casing 81 (second housing portion), the first lead electrode 14, the second lead electrode 15, the third lead electrode 16, the fourth lead electrode 17, the first quartz substrate 8, the second quartz substrate 9, the O-ring 12c, the flange 13 and the flange ring 23.

The QCM sensor body 2 according to the embodiment does not include the O-rings 12a, 12b, the spacers 11 and the screws (refer to FIG. 3) provided in the first embodiment. Concerning a contact portion between the first casing 80 and the first quartz substrate 8 in the QCM sensor body 2 according to the embodiment, the first casing 80 and the first quartz substrate 8 are directly bonded. Similarly, concerning a contact portion between the second casing 81 and the second quartz substrate 9, the second casing 81 and the second quartz substrate 9 are directly bonded. Furthermore, the first casing 80 and the second casing 81 are also directly bonded. The first casing 80 and the second casing 81 are made of a material such as PDMS (dimethylpolysiloxane), which can activate atomic bonding with respect to the quartz substrates by short-wavelength light. The PDMS is activated on the surface thereof by short-wavelength light such as UV (ultraviolet) light and becomes in a state of being bonded to a Si element easily. In a step of assembling the first casing 80 and the first quartz substrate 8, the contact portion between the first casing 80 and the first quartz substrate 8 is irradiated by short-wavelength light to thereby activate the surface, then, the first casing 80 is bonded to the first quartz substrate 8 (for example, called siloxane bond). Accordingly, it is possible to prevent the measurement sample from entering the housing even when a sealing material such as the O-ring is not used. The same bonding is performed also between the second casing 81 and the second quartz substrate 9. Moreover, a contact portion between the first casing 80 to which the first quartz substrate 8 is bonded and the second casing 81 to which the second quartz substrate 9 is bonded is irradiated by short-wavelength light to thereby activate the surface, then, the first casing 80 is bonded to the second casing 81. As the first quartz substrate 8 and the second quartz substrate 9 are respectively bonded to and held by the first casing 80 and the second casing 81, a space (isolation layer 26) between the first quartz substrate 8 and the second quartz substrate 9 can be formed when the first casing 80 is bonded to the second casing 81 as well as the first quartz substrate 8 and the second quartz substrate 9 face each other, therefore, the spacers 11 are not necessary. Additionally, it becomes easy to fabricate the QCM sensor body 2 after performing assembly of the first casing 80 and the quartz crystal vibrator for measurement in a different process from assembly of the second casing 81 and the quartz crystal vibrator for reference as described above. Accordingly, positional accuracy between the quartz crystal vibrator for measurement and the quartz crystal vibrator for reference can be adjusted by relative positions of the first casing 80 and the second casing 81, therefore, mutual arrangement between the quartz crystal vibrator for measurement and the quartz crystal vibrator for reference and/or adjustment of the shape, capacity and so on of the space between the quartz crystal vibrator for measurement and the quartz crystal vibrator for reference can be easily performed.

As the first casing 80 and the second casing 81 are made of the material such as PDMS (dimethylpolysiloxane), which can activate atomic bonding with respect to the quartz substrates by short-wavelength light as described above, the number of parts can be reduced while securing vibration of the quartz crystal vibrators. Moreover, the O-ring, the spacer and so on for supporting the quartz crystal vibrator with respect to the housing are not necessary, and variations in vibration of the quartz crystal vibrators caused by variations in arrangement can be reduced, therefore, measurement can be performed more accurately.

What is claimed is:

1. A QCM sensor for detecting a physical quantity of a sample by allowing the sample to contact an excitation electrode on a surface of a quartz crystal vibrator, comprising:
    a quartz crystal vibrator for measurement having a first electrode which can be contacted by a measurement sample to be detected and having a first quartz substrate with a surface on which the first electrode is formed;
    a quartz crystal vibrator for reference having a second electrode which can be contacted by a reference sample as a reference when detecting a physical quantity of the measurement sample and having a second quartz substrate with a surface on which the second electrode is formed;

a housing accommodating the quartz crystal vibrator for measurement and the quartz crystal vibrator for reference, the housing having opposite ends and an opening in one of the ends through which the first electrode is exposed for contacting the measurement sample; and a confining portion at the other end of the housing and confining the reference sample in the housing in a state of contacting the second electrode.

2. The QCM sensor according to claim 1, wherein the confining portion is formed inside an outline of the quartz crystal vibrator for reference when seen from a direction perpendicular to the surface of the quartz crystal vibrator for reference.

3. The QCM sensor according to claim 1, wherein the confining portion is formed in an opening in the other end of the housing so as to confine the reference sample in a thickness of the housing when seen from a direction parallel to the surface of the quartz crystal vibrator for reference.

4. The QCM sensor according to claim 1, further comprising a third electrode formed on an opposite surface of the surface on which the first electrode is formed in the first quartz substrate and a fourth electrode formed on an opposite surface of the surface on which the second electrode is formed in the second quartz substrate; and wherein the housing is formed so as to accommodate the third electrode and the fourth electrode in a common space.

5. The QCM sensor according to claim 4, wherein the quartz crystal vibrator for measurement and the quartz crystal vibrator for reference are arranged so that the third electrode faces the fourth electrode, and the housing supports the quartz crystal vibrator for measurement and the quartz crystal vibrator for reference so that the third electrode and the fourth electrode have a given gap therebetween.

6. The QCM sensor according to claim 1, wherein the reference sample is formed by confining the measurement sample in an initial state by the confining portion.

7. The QCM sensor according to claim 1, further comprising a seal accommodated inside of the housing together with the quartz crystal vibrator for measurement and the quartz crystal vibrator for reference for preventing the entry and leakage of the measurement and reference samples to and from the inside of the housing.

8. The QCM sensor according to claim 7, wherein the seal comprises at least two O-rings.

9. The QCM sensor according to claim 7, wherein the seal comprises a silicone resin sealant.

10. A QCM sensor for detecting a physical quantity of a sample by allowing the sample to contact an excitation electrode on a surface of a quartz crystal vibrator, comprising:

a quartz crystal vibrator for measurement having a first electrode which can be contacted by a measurement sample to be detected and having a first quartz substrate with a surface on which the first electrode is formed;

a quartz crystal vibrator for reference having a second electrode which can be contacted by a reference sample as a reference when detecting a physical quantity of the measurement sample and having a second quartz substrate with a surface on which the second electrode is formed;

a housing accommodating the quartz crystal vibrator for measurement and the quartz crystal vibrator for reference, the housing having a higher thermal conductivity than a thermal conductivity of the reference sample; and a confining portion connected to the housing and confining the reference sample in the housing in a state of contacting the second electrode.

11. A QCM sensor for detecting a physical quantity of a sample by allowing the sample to contact an excitation electrode on a surface of a quartz crystal vibrator, comprising:

a quartz crystal vibrator for measurement having a first electrode which can be contacted by a measurement sample to be detected and having a first quartz substrate with a surface on which the first electrode is formed;

a quartz crystal vibrator for reference having a second electrode which can be contacted by a reference sample as a reference when detecting a physical quantity of the measurement sample and having a second quartz substrate with a surface on which the second electrode is formed;

a housing accommodating the quartz crystal vibrator for measurement and the quartz crystal vibrator for reference, the housing having a higher thermal conductivity than thermal conductivities of the quartz crystal vibrator for measurement and the quartz crystal vibrator for reference; and a confining portion connected to the housing and confining the reference sample in the housing in a state of contacting the second electrode.

12. A QCM sensor for detecting a physical quantity of a sample by allowing the sample to contact an excitation electrode on a surface of a quartz crystal vibrator, comprising:

a quartz crystal vibrator for measurement having a first electrode which can be contacted by a measurement sample to be detected and having a first quartz substrate with a surface on which the first electrode is formed;

a quartz crystal vibrator for reference having a second electrode which can be contacted by a reference sample as a reference when detecting a physical quantity of the measurement sample and having a second quartz substrate with a surface on which the second electrode is formed;

a housing accommodating the quartz crystal vibrator for measurement and the quartz crystal vibrator for reference;

a confining portion connected to the housing and confining the reference sample in the housing in a state of contacting the second electrode; and a first O-ring provided at the first electrode and a second O-ring provided at the second electrode for preventing the entry and leakage of the measurement and reference samples to and from the inside of the housing.

13. The QCM sensor according to claim 12, further comprising: a third electrode formed on a surface of the first quartz substrate opposite to the surface thereof on which the first electrode is formed; a fourth electrode formed on a surface of the second quartz substrate opposite to the surface thereof on which the second electrode is formed; first and second lead electrodes connected to the quartz crystal vibrator for measurement; and third and fourth lead electrodes connected to the quartz crystal vibrator for reference; and wherein the quartz crystal vibrator for measurement and the quartz crystal vibrator for reference are fixed to the housing only by the first and second O-rings and the first, second, third and fourth lead electrodes.

14. A QCM sensor for detecting a physical quantity of a sample, the QCM sensor comprising:

a quartz crystal vibrator for measurement having a first quartz substrate and a first electrode formed on the first quartz substrate for contacting a measurement sample whose physical quantity is to be detected;

a quartz crystal vibrator for reference having a second quartz substrate and a second electrode formed on the second quartz substrate for contacting a reference sample as a reference when detecting the physical quantity of the measurement sample;

a housing accommodating the quartz crystal vibrator for measurement and the quartz crystal vibrator for reference; and seals provided in the housing at the first and second electrodes and on surfaces of the first and second quartz substrates for preventing leakage of the measurement sample and the reference sample from the inside of the housing.

15. The QCM sensor according to claim 14, wherein the seals comprise a first O-ring provided on the surface of the first quartz substrate and a part of the first electrode, and a second O-ring provided on the surface of the second quartz substrate and a part of the second electrode.

16. The QCM sensor according to claim 14, wherein each of the seals is a silicone resin sealant.

17. The QCM sensor according to claim 14, wherein the housing has a higher thermal conductivity than a thermal conductivity of the reference sample.

18. The QCM sensor according to claim 14, wherein the housing has a higher thermal conductivity than thermal conductivities of the quartz crystal vibrator for measurement and the quartz crystal vibrator for reference.

* * * * *